United States Patent

Nemoto et al.

Patent Number: 5,922,582
Date of Patent: Jul. 13, 1999

[54] INDOLE ALKALOID TYPE COMPOUND 0089-D

[75] Inventors: Akira Nemoto, Ibaraki-ken; Yasushi Tanaka, Chiba-ken; Hisayuki Komaki, Chiba-ken; Yuzuru Mikami, Chiba-ken; Katsukiyo Yazawa, Chiba-ken; Jun'ichi Kobayashi, Hokkaido, all of Japan

[73] Assignee: HIGETA SHOYU Co., Ltd., Tokyo, Japan

[21] Appl. No.: 09/054,514

[22] Filed: Apr. 3, 1998

Related U.S. Application Data

[51] Int. Cl.$^6$ .......................... A61K 31/40; C07D 209/08
[52] U.S. Cl. ........................... 435/121; 514/415; 548/505
[58] Field of Search .............................. 514/415; 548/505

[56] References Cited

U.S. PATENT DOCUMENTS 5,468,898  11/1995  Huang et al. ............................ 560/450

FOREIGN PATENT DOCUMENTS

09309861 A   2/1997   Japan .

OTHER PUBLICATIONS

"The Essentials of Antibiotics", 4th Edition, Tokyo University Press, 1992.
Y. Mikami et al; Susceptibility Patterns of Pathogenic Nocardia to Some Selected Antimicrobial Agents and their Usefulness in the Identification of Work in a Clinical Laboratory; Bull. JFCC, vol. 5, 89–95, 1989.

*Primary Examiner*—Joseph K. McKane
*Attorney, Agent, or Firm*—Browdy and Neimark

[57] ABSTRACT

The present invention relates to compound 0089-D having excellent antitumor activity and antimicrobial activity, represented by the general formula (I):

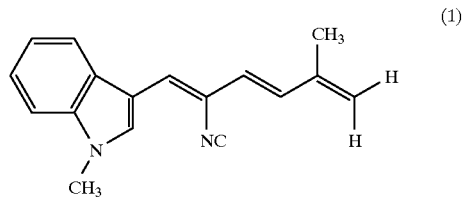

or pharmaceutically acceptable salts thereof.

4 Claims, No Drawings

INDOLE ALKALOID TYPE COMPOUND 0089-D

DETAILED DESCRIPTION OF THE INVENTION

1. Technical Field to Which the Invention Belongs

The present invention relates to novel compound 0089-D and a process for producing the same, as well as uses thereof. The novel compound 0089-D is an unknown novel indole alkaloid type compound isolated and purified from a culture of microorganisms, particularly actinomycetes, and has excellent physiological activity, particularly excellent antitumor activity and antimicrobial activity.

Accordingly, the novel indole alkaloid type compound of the present invention can be utilized effectively as an antitumor agent and antimicrobial agent as a preventive and/or therapeutic agent for such diseases.

2. Prior Art

A large number of novel compounds have been discovered as antitumor agents and antimicrobial agents and novel compounds have also been synthesized, and some of them are practically used.

Among conventionally known antitumor agents and antimicrobial agents, there are certainly several types of excellent agents, but there is demand for further development not only for effect but also for safety and productivity.

3. Problem to Be Solved by the Invention

The present invention was made to respond to such demand in this field and as a result of extensive screening in line with technical development of antitumor agents and antimicrobial agents, the present inventors found that a novel compound not known up to now has antitumor activity and antimicrobial activity, thereby completing the present invention. The present invention was made for the purpose of providing a novel compound having superior antitumor activity and antimicrobial activity to known substances.

4. Means to Solve the Problem

For the purpose of obtaining a novel substance having antitumor activity, the present inventors screened a wide variety of natural substances, particularly metabolites from microorganisms, and as a result of screening for substances having more effective antitumor activity, they found that novel *Nocardia brasiliensis* IFM 0089 (FERM BP-5542) produces and accumulates a substance with the desired properties in the cells. By revealing its chemical structure, they confirmed this substance to be a novel substance not known up to now, and this substance was designated 0089 and a patent application thereto was filed (JP-A 9-309861 (1997)).

This time, the present inventors have further examined the mycerial extract of *Nocardia brasiliensis* IFM 0089, and as a result, they found a substance with antitumor activity and antimicrobial activity different from those of the above compound 0089, and they confirmed this substance to be a novel substance not known up to now by further examining its physicochemical properties in detail and revealing its chemical structure. This substance was a novel compound of indole alkaloid type represented by the general formula (1) as recited in claim 1. The present inventors have designated this compound 0089-D.

That is, the present invention relates to novel compound 0089-D represented by the general formula (1):

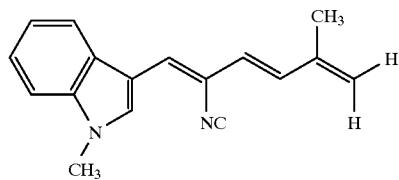

(1)

or pharmaceutically acceptable salts thereof.

The present invention further relates to a novel antitumor agent and antimicrobial agent comprising the novel indole alkaloid type compound 0089-D or a pharmaceutically acceptable salt thereof as an effective ingredient. Hereinafter, the present invention is described in detail.

EMBODIMENTS FOR CARRYING OUT THE INVENTION

The physicochemical properties of compound 0089-D of the present invention are shown in Table 1 below.

TABLE 1

Physicochemical Properties of Compound 0089-D
(1) Color and state of the substance: yellow solid
(2) Infrared absorption spectrum:
   Its significant signals are as follows:
   IR (film) ν: 2955, 2925, 2105, 1595, 1520, 1475, 1380, 1245, 1120, 1065, 740 cm$^{-1}$
(3) Ultraviolet absorption spectrum:
   Its significant signals are as follows:
   UV (EtOH) $\lambda_{max}$: 332 ($\epsilon$20000), 275 (35000), 268 (40000), 220 (sh), 204 (18000) nm
(4) Molecular weight: 248
(5) Molecular formula: $C_{17}H_{16}N_2$
(6) Mass spectrum:
   EIMS m/z: 248 (M$^+$)
   HREIMS m/z Found: 248.1316 (M$^+$)
   Calculated: 248.1316 ($C_{17}H_{16}N_2$)
(7) $^1$H nuclear magnetic resonance spectrum:
   Its significant signals are as shown in Table 2.
(8) $^{13}$C nuclear magnetic resonance spectrum:
   Its significant signals are as shown in Table 2.
(9) Solubility:
   Soluble in methanol, ethyl acetate and ether.
   Slightly soluble in hexane.
   Insoluble in water.
   Significant signals in $^1$H NMR and $^{13}$C NMR spectra of 0089-D in Table 2.

TABLE 2

$^1$H and $^{13}$C NMR data of Compound 0089-D (CDCl$_3$) (a: δ [in ppm])

| Position | $^1$H$^{a)}$ | J (Hz) | $^{13}$C$^{a)}$ |
|---|---|---|---|
| 2 | 8.06s | | 130.6d |
| 3 | | | 109.7s |
| 4 | | | 127.8s |
| 5 | 7.69brd | 8.1 | 118.1d |
| 6 | 7.23brd | 1.0, 7.0, 8.0 | 120.7d |
| 7 | 7.31brd | 1.0, 7.1, 8.0 | 123.0d |
| 8 | 7.37brd | 8.1 | 109.8d |
| 9 | | | 136.3s |

TABLE 2-continued $^1$H and $^{13}$C NMR data of
Compound 0089-D (CDCl$_3$) (a: δ [in ppm])

| Position | $^1$H$^{a)}$ | J (Hz) | $^{13}$C$^{a)}$ |
|---|---|---|---|
| 10 | 6.82brs | | 121.3d |
| 11 | | | 118.1s |
| 12 | 6.25d | 15.3 | 123.4d |
| 13 | 6.65d | 15.3 | 131.7d |
| 14 | | | 141.0s |
| 15(a) | 5.19s | | 118.5t |
| 15(b) | 5.11s | | |
| 16 | 1.96brs | | 18.8q |
| 17 | 3.88s | | 33.4q |
| 18 | | | 169.7s |

Compound 0089-D of the present invention is produced by, e.g. *Nocardia brasiliensis* IFM 0089 (FERM BP-5542).

The microbiological characteristics of *Nocardia brasiliensis* IFM 0089 are that morphologically it has branched long hyphae and aerial hyphae as observed in one kind of actinomycetes when cultured in an oatmeal agar medium (ISP-3). By extending the culture time, a few of bacilliform spores and fragmentation of aerial hyphae and vegetative hyphae were observed. Since the fragmentation of vegetative hyphae was observed, it was estimated morphologically to belong to the genus Nocardia.

The cultural characteristics of *Nocardia brasiliensis* IFM 0089 in various media are shown in Table 3 below. The physiological and biochemical characteristics are shown in Table 4 below.

TABLE 3

Cultural Characteristics of *Nocardia brasiliensis* IFM 0089

| Medium | Characteristics |
|---|---|
| ISP-2 (yeast extract/malt extract agar) | vigorous growth, wrinkles on the surface, brown vigorous white aerial hyphae |
| ISP-3 (oatmeal agar) | moderate growth, smooth surface, whitish yellow vigorous white aerial hyphae |
| ISP-4 (starch/inorganic salt agar) | no or little growth |
| ISP-5 (glycerin/asparagine agar) | moderate growth, smooth surface, brown trace aerial hyphae |
| ISP-6 (peptone/yeast extract iron agar) | trace growth, wrinkles on the surface, brown |
| BHI (brain heart infusion agar) | vigorous growth, wrinkles on the surface, orange color |
| SDA (Sabouraud's dextrose agar) | vigorous growth, wrinkles on the surface, orange color trace aerial hyphae |

TABLE 4

Physiological and Biochemical Characteristics of *Nocardia brasiliensis* IFM 0089

Decomposition ability:

| | |
|---|---|
| adenine | negative |
| casein | positive |
| hypoxanthine | positive |
| tyrosine | positive |
| xanthine | negative |

TABLE 4-continued

Physiological and Biochemical Characteristics of *Nocardia brasiliensis* IFM 0089

Production of acid from sugar:

| | |
|---|---|
| galactose | positive |
| glucose | positive |
| inositol | positive |
| rhamnose | negative |
| maltose | negative |
| adonitol | negative |
| arabinose | negative |
| erythritol | negative |
| mannose | negative |
| sorbitol | negative |
| Utilization of citric acid: | positive |

Susceptibility to antibiotics:

| | |
|---|---|
| imipenem | negative |
| tobramycin | positive |
| 5-FU | negative |
| kanamycin | negative |
| β-Lactamase production: | positive |
| Growth limit temperature: | not growing at 45° C. |

The present strain was cultured in a medium (brain heart infusion containing 2% glucose) at 250 rpm at 30° C. for 72 hours with shaking, and the cells grown in the medium was harvested by centrifugation (3000 rpm×10 minutes) and washed twice with distilled water. Further, the cells were washed with ethanol and then dried under vacuum to give the dried cells. The amino acid composition, sugar composition and lipid composition of the cell wall of this dried cells were examined on the basis of Bergey's Manual of Determinative Bacteriology, 9th ed., Williams, Baltimore, 1993. Meso-diaminopimelic acid was detected in the amino acid analysis, and arabinose and galactose were detected in the sugar analysis. The presence of mycolic acid was confirmed from the result of the lipid analysis, and its type was Nocardia type. Isoprenoid quinone, i.e., a cell lipid component was confirmed to contain MK-8 (H4) cycle as a major component. The present strain was identified as *Nocardia brasiliensis*, further from its ability to assimilate casein, hypoxanthine and tyrosine and from its production pattern of acid from sugar and its susceptibility pattern to antimicrobial agents as shown in Table 4 (Mikami & Yazawa, Susceptibility pattern of pathogenic Nocardia to some selected antimicrobial agents and their usefulness in the identification work in a clinical laboratory: Bull. JFCC "Bulltein of the Japan Federation for Culture Collections", 5: 89–95, 1989).

The present strain is thus classified into *Nocardia brasiliensis* and designated *Nocardia brasiliensis* IFM 0089, and it was deposited under FERM BP-5542 on May 16, 1996 under the Budapest Treaty with the National Institute of Bioscience and Human-Technology, Agency of Industrial Science and Technology, Japan.

It has been confirmed that compound 0089-D of the present invention is produced not only by *Nocardia brasiliensis* IFM 0089 (FERM BP-5542) but also by other strains belonging to the genus Nocardia, and production of compound 0089-D in the present invention encompasses use of a wide variety of all mutants capable of producing compound 0089-D, including artificial mutants obtainable from these microorganisms by subjecting them to mutation treatment using X-ray irradiation, γ-ray irradiation, nitrogen mustard, N-methyl-N'-nitro-N-nitrosoguanidine, 2-aminopurine, ethylmethane sulfonate, etc. as well as natural mutants.

The novel compound 0089-D of the present invention represented by the general formula (1) can be produced not only by chemical synthesis methods but also by microorganisms as described above.

In the latter case, the novel compound 0089-D of the present invention represented by the general formula (1) can be produced by culturing a microorganism producing said compound and belonging to the genus Nocardia, such as *Nocardia brasiliensis* IFM 0089, in a medium containing a carbon source and a nitrogen source capable of being assimilated by the microorganism, preferably under aerobic submerged culture conditions (e.g., shake culture, agitated and aerated fermentation, etc.).

The carbon source used is preferably glucose, glycerol, sucrose, starch, dextrin and other carbohydrates.

The nitrogen source used is preferably oatmeal, yeast extract, beef extract, tuna meat extract, peptone, gluten meal, cottonseed powder, soybean meal, corn steep liquor, dried yeast, wheat germ, peanut powder, chicken bone meat meal, etc., and further inorganic and organic nitrogen-containing compounds such as ammonium salts (e.g., ammonium nitrate, ammonium sulfate, ammoniumphosphate, etc.), urea, amino acids, etc. can also be used advantageously.

Although it is advantageous to use these carbon and nitrogen sources in combination, these are not necessarily pure for use. This is because some impure sources contain a trace amount of growth factors so their use is desired.

If necessary, inorganic salts such as sodium carbonate, potassium carbonate, sodium phosphate, potassium phosphate, sodium chloride, potassium chloride, sodium iodide, potassium iodide, magnesium salts, copper salts, cobalt salts, etc. can be added to the medium.

If necessary, particularly where the medium will foam, an antifoaming agent such as fluid paraffin, animal oil, vegetable oil, mineral oil, silicone, etc. can be added.

For large-scale industrial production of the object substance, the microorganism is cultured preferably under aeration with agitating in a manner similar to production of other fermentation products. For small-scale production, shake culture using a flask is preferable.

If culture is conducted in a large tank, it is preferred that the producing microorganism is first inoculated into a relatively small amount of medium and cultured in it, and the culture is then transferred to a large production tank where the microorganism is cultured, thus preventing the growth of the microorganism from being delayed in the step of producing compound 0089-D.

In this case, the medium composition used for pre-culture and that for production culture may be the same or may be different if necessary.

Culture is carried out preferably under aeration with agitating by known methods using e.g., propellers and other apparatuses, rotation or shake in a fermenter, pump processing, air blowing, etc. Air for aeration is preferably sterilized.

Although the culture temperature may be altered suitably within the range in which the 0089-D-producing microorganism produces said compound, the microorganism is cultured usually at 10 to 40° C., preferably 25 to 35° C.

Although the period of culture varies depending on culture conditions and culture volume, the period is usually about 1 day to 1 week.

After fermentation is finished, the desired compound 0089-D is recovered from the culture. That is, the cells are subjected directly to extraction with water or organic solvent, or is first disrupted mechanically or by known means such as ultrasonication, etc. and then subjected to extraction with water and/or organic solvent, followed by recovery and purification according to conventional methods. In the case of culture broth, direct extraction with solvent may be conducted, or the culture broth may be filtered or centrifuged, concentrated under reduced pressure and lyophilized, and after pH adjustment is conducted, the sample is applied and adsorbed onto carrier such as anion or cation exchange resin, activated carbon, powder cellulose, silicagel, alumina, adsorption resin, etc., followed by elution of compound 0089-D from the carrier.

As the recovery and purification methods, conventional methods for recovery of antibiotics are suitably used, including solvent extraction with water, organic solvents, or a mixed solvent thereof; chromatography; recrystalization from a single solvent or a mixed solvent; and a combination thereof.

The recovery and purification of compound 0089-D is carried out by suitable use of the known methods described above, for example as follows:

First, the cells are collected by centrifuging the culture or treating it with an MF membrane, followed by extraction with methanol, and this extract fraction is further extracted with n-hexane, concentrated under reduced pressure, subjected to silica gel chromatography for adsorption, subjected to step-wise elution with hexane-ethyl acetate for fractionational purification, concentrated under reduced pressure and evaporated into dryness.

In the case of administering compound 0089-D of the present invention as a pharmaceutical preparation, the compound of the present invention is administered as such or as a pharmaceutical composition containing the compound at e.g., 0.1 to 99.5%, preferably 0.5 to 90% in pharmaceutically acceptable non-toxic and inert carrier.

As the carrier, use is made of at least one of solid, semi-solid or liquid diluents, fillers, and other aids for formulation. The pharmaceutical composition is administered preferably in a dosage unit form. The pharmaceutical composition of the present invention can be administered through oral administration, intra-tissue administration, topical administration (transdermal administration, etc.), or through the rectum, but it can also be used as an agent for external application. As a matter of course, the composition should be administered in preparation forms suitable for these administration methods.

Although the dosage thereof as an antitumor agent or antimicrobial agent is regulated preferably depending on conditions such as the age, weight, etc. of the patient, administration route, and the type, severeness, etc. of the disease, a usual dosage for an adult is in the range of about 10 to 2000 mg/day as the amount of the effective ingredient of the present invention. A lower dosage than this range may suffice in some cases, and a higher dosage may be necessary in other cases. If administered in a large amount, it is administered desirably in portions at intervals per day.

Oral administration can be carried out using a solid or liquid dosage unit, for example in the form of powder, mixed powder, tablet, sugar-coated tablet, capsule, drop, sublingual tablet, etc.

The powder is produced by dividing the present compound into powder of suitable size. The mixed powder is produced by dividing the present compound into powder of suitable size and then mixing it with similarly divided pharmaceutical carrier such as eatable carbohydrates such as starch, mannitol, etc. Flavoring, preservative, suspending agent, coloring agent, perfume, etc. may also be mixed as necessary.

The capsule is produced by charging capsule outer cover such as gelatin capsules with the powder, the mixed powder or the granules of the present compound. The present compound in the form of, e.g., powder may be filled into such outer cover after it was mixed with lubricant or fluidity agent, such as colloidal silica, talc, magnesium stearate, calcium stearate and solid polyethylene glycol. Addition of disintegrating agent or solubilization agent such as carboxymethylcellulose, calcium carbonate and sodium carbonate can improve the efficacy of the pharmaceutical preparation when taken in the form of capsule.

In addition, the finely divided powder of the present compound may be formed into soft capsule by suspending and dispersing it in vegetable oil, polyethylene glycol, glycerin, or a surface active agent and covering the mixture with a gelatin sheet.

The tablet is produced by preparing a powder mixture containing the present compound, granulating or slagging it and then adding a disintegrating agent or lubricant to it, followed by tabletting.

The powder mixture is produced by mixing the suitably powdered present compound with the above diluent or base, and if necessary, binder (e.g., sodium carboxymethylcellulose, alginate, gelatin, polyvinyl pyrrolidone, polyvinyl alcohol, etc.), dissolution-delaying agent (e.g., paraffin, etc.), re-absorber (e.g., quaternary salts) and/or absorption agent (e.g., bentonite, kaolin, dicalcium phosphate) may be used in combination. The powder mixture can be formed into granules by first moistening it with a binder such as syrup, starch paste, gum Arabic, cellulose solution or polymer solution and then enforceably passing it through a screen. Instead of granulating it in this manner, the powder can be formed into granules in an alternative manner by introducing it into a tabletting machine and disrupting the resulting slag in an incomplete form into granules.

The granules produced in this manner can be prevented from adhering to one another by adding stearic acid, stearate, talc, mineral oil, etc. as lubricant. The mixture thus lubricated is then tabletted. Also, the present compound may be tabletted directly after it was combined with fluid inert carrier, without forming it into granules or slag as described above. Use can be made of transparent or semi-transparent protective coating made of shellac sealed coating, coating of sugar or polymeric material, and polished coating made of wax.

Other oral administration forms, such as solution, syrup, elixir, etc. can also be formed in a dosage unit form so as to contain a predetermined amount. The syrup is produced by dissolving the present compound in a suitable aqueous perfuming solution, and the elixir is formulated by suspending the present compound in non-toxic alcoholic carrier. The solubilization agent or emulsifying agent (e.g., ethoxylated isostearyl alcohols, polyoxyethylene sorbitol esters), preservative, flavor-imparting agent (e.g., peppermint oil, saccharin) and others can also be added as necessary.

If necessary, the dosage unit formulation for oral administration may be formed into microcapsule. This formulation can be coated or filled in polymer, wax, etc. to extend its acting period or to achieve sustained release.

Parenteral administration can be effected using a liquid dosage unit form for intradermal, intramuscular or intravenous injection, for example in the form of solution or suspension. These are produced by suspending or dissolving a predetermined amount of the present compound in non-toxic liquid carrier, e.g., aqueous or oily media suited to the object of injection and then sterilizing the resulting suspension or solution. Alternatively, a predetermined amount of the present compound is placed in a vial and then the vial and its content may be sterilized and sealed. To dissolve or mix it just before administration, preliminary vial or carrier may be prepared along with the powdered or lyophilized effective ingredient. A non-toxic salt or salt solution may be added to render the injection isotonic. Further, stabilizer, preservative, emulsifying agent, etc. can be used in combination.

Administration into the rectum can be effected using suppository in which low-melting solid, such as polyethylene glycol, cacao lipid, higher esters (e.g., myristyl palmitinate) and salt thereof is mixed.

Hereinafter, the present invention is described in more detail with reference to the Examples, which however not are intended to limit the present invention.

EXAMPLE 1

(1) Production by Fermentation

*Nocardia brasiliensis* IFM 0089 (FERM BP-5542) was inoculated into 25 ml brain heart infusion liquid medium (Difco) containing 2% glucose in a 50-ml Erlenmeyer flask and cultured at 30° C. for 72 hours with shaking. 2 ml of the culture was inoculated into 200 ml of the same medium in a 500-ml Erlenmeyer flask and pre-cultured in the same manner as above. The resulting pre-culture, 1.5 L, was further inoculated into a 200-L tank fermenter containing 150 L production medium, pH 7.0 containing 2% glucose, 0.5% meat extract (Wako Pure Chemical Industries, Ltd.), 0.5% polypeptone P1, 0.5% polypeptone (Nippon Seiyaku K.K.) and 0.3% sodium chloride and cultured at an aeration rate of 150 L/min. at an agitation rate of 200 rpm at 28° C. for 90 hours.

(2) Recovery and Purification

The resulting culture, 150 L, was filtered through a filter cloth whereby the cells were recovered. The operation of extracting the cells was carried out by adding 20 L methanol. The thus-obtained extract was concentrated and evaporated into dryness in an evaporator. 1 L distilled water was added to 4 g of the dried matter to give a suspension, which was then partitioned and extracted 3 times with 1 L of n-hexane. The n-hexane fraction, 3 L, was concentrated and evaporated into dryness in an evaporator, dissolved in 8 ml of an n-hexane:ethyl acetate mixture (20:1) and subjected to silica gel chromatography (column 6 cm×20 cm). After impurities were eluted with 2 L of an n-hexane : ethyl acetate mixture (20 1), compound 0089-D was eluted with 2 L of an n-hexane:ethyl acetate mixture (10:1). Detection of compound 0089-D in the eluted fraction was carried out using growth inhibitory activity on a test microorganism *Micrococcus luteus* as the indicator by the following paper disk method.

The eluted fraction was adsorbed onto a paper disk and placed on a nutrient agar medium (Difco) on which *M. luteus* had been spread, and then incubated at 30° C. for 24 hours. The presence of compound 0089-D was indicated by the inhibition zone of growth of *M. luteus* on the medium.

Fractions having growth inhibitory activity on *M. luteus* were collected, concentrated and evaporated into dryness in an evaporator to give 30 mg of a purified preparation of compound 0089-D.

EXAMPLE 2

Antitumor Activity

Cytotoxicity of compound 0089-D on cultured tumor cell lines, P388, adriamycin resistant P388 (P388/ADR), L1210 and KB was examined in the following manner.

L1210 was suspended in RPMI1640 medium, P388 and P388/ADR in RPMI1640 medium containing 20 $\mu$M of 2-mercaptoethanol, and KB in Dulbecco's MEM medium (any medium contained 10% fetal bovine serum) respectively whereby cell suspension ($5.6 \times 10^4$ cells/ml) were prepared. The test sample was dissolved in methanol and diluted serially with each medium to give solutions containing the test sample at various concentrations. 180 μl of the cell suspension and 20 μl of the test sample solution were put through a pipette to a 96-well micro-titer plate and incubated in a wet atmosphere of 5% $CO_2$/95% air at 37° C. 72 hours thereafter, cell growth was measured by the following calorimetric assay method using 3-(4,5-dimethyl-2-thiazolyl)-2,5-diphenyl-2H-tetrazolium bromide (MTT).

That is, 20 μl of 2 mg/ml MTT solution was added to each well and the cells were incubated for 4 hours at 37° C. Thereafter, 50 μl of 50% dimethylformamide solution containing 20% sodium dodecyl sulfate was added to each well to dissolve the formed violet formazan crystal, and its absorbance at 570 nm was measured in a microplate reader (immunoreader) and used as an indicator of the growth. Degree of growth inhibition was calculated using the following equation, and the concentration of the test sample at which the growth of cells was inhibited by 50% ($IC_{50}$) was determined from the relationship between the test sample concentration and degree of inhibition.

Degree of inhibition=[1—(absorbance in the presence of test sample)/(absorbance in the absence of test sample)]×100

As a result, the $IC_{50}$ value of the present compound was 0.25 μg/ml for L1210, 0.44 μg/ml for P388, 0.56 μg/ml for P388/ADR, and 0.75 μg/ml for KB, indicating that compound 0089-D has strong cytotoxicity (÷antitumor activity) on the cultured tumor cells (Table 5).

TABLE 5

Inhibitory Activity of Compound 0089-D on Growth of Tumor Cells

| Cell lines | $IC_{50}$ (μg/ml) 0089-D |
|---|---|
| L1210 | 0.25 |
| P388 | 0.44 |
| adriamycin-resistant P388 | 0.56 |
| KB | 0.75 |

EXAMPLE 3

Antimicrobial Activity

The antimicrobial activity of compound 0089-D on various microorganisms was confirmed by determining minimum inhibitory concentration (MIC) on growth.

The MIC of compound 0089-D for various microorganisms was determined in a Muller Hinton broth (BBL) containing 0.2% glucose according to the regulations of the Japan Chemotherapy Association (The Essentials of Antibiotics, 4th ed., Tokyo University Press, 1992).

Each test microorganism was prepared at density of $1 \times 10^6$ cfu/ml in the above medium to prepare a test microorganism liquid.

To determine MIC for fungi, Sabouraud's Dextrose liquid medium was used and the density of the test fungi was $1 \times 10^4$ cfu/ml.

The test sample (compound 0089-D) was dissolved in methanol and diluted in the above Muller Hinton broth by subjecting it to serial 2-fold dilution starting at the concentration of 1 mg/ml. 180 μl of the test microorganism liquid and 20 μl of the test sample solution were put through a pipette to a 96-well micro-titer plate and incubated at 37° C. 24 hours thereafter, growth was examined by the eye to determine MIC.

Compound 0089-D demonstrated a wide antimicrobial spectrum (Table 6).

TABLE 6

Antimicrobial Activity of Compound 0089-D

| Test Microorganism | MIC (μg/ml) |
|---|---|
| Micrococcus luteus IFM2066 | 3.13 |
| Bacillus subtilis PCI189 | 3.13 |
| Nocardia transvalensis IFM0333 | 3.13 |
| N. pseudobrasiliensis IFM0624 | 3.13 |
| N. brasiliensis IFM0236 | 25 |
| N. otitidiscaviarum IFM0239 | 6.25 |
| N. nova IFM0290 | 1.56 |
| N. asteroides IFM0319 | 12.5 |
| N. farcinica IFM0284 | 12.5 |
| Mycobacterium smegmatis ATCC607 | 0.78 |
| M. phlei ATCC11758 | 1.56 |
| M. flavescens ATCC14474 | 3.13 |
| Aspergillus niger ATCC40606 | 0.39 |
| Candida albicans ATCC90028 | 25 |

EFFECT OF THE INVENTION

The present invention provides compound 0089-D, and the present compound is a novel compound, has excellent physiological activity, and can be utilized in various pharmaceutical preparations such as antitumor agent, antimicrobial agent, etc.

What is claimed is:

1. A compound represented by the general formula (1):

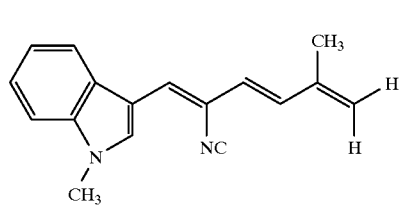

(1)

or a pharmaceutically acceptable salt thereof.

2. An antitumor composition comprising the compound as described in claim 1 or a pharmaceutically acceptable salt thereof as an effective ingredient and a pharmaceutically acceptable carrier.

3. An antimicrobial composition comprising the compound as described in claim 1 or a pharmaceutically acceptable salt thereof as an effective ingredient and a pharmaceutically acceptable carrier.

4. A process for producing the compound as described in claim 1 or salts thereof, which comprises culturing a microorganism belonging to the genus Nocardia to produce said compound, and recovering said compound from the culture.

* * * * *